United States Patent [19]
Chang et al.

[11] 4,220,783
[45] Sep. 2, 1980

[54] SYNTHESIS OF PYRIDINE AND ALKYLPYRIDINES

[75] Inventors: Clarence D. Chang, Princeton; William H. Lang, Pennington, both of N.J.

[73] Assignee: Mobil Oil Corporation, New York, N.Y.

[21] Appl. No.: 37,265

[22] Filed: May 9, 1979

[51] Int. Cl.$^2$ ................... C07D 213/08; C07D 213/10
[52] U.S. Cl. ..................................... 546/251; 546/254
[58] Field of Search ............................... 546/251, 254

[56] References Cited

U.S. PATENT DOCUMENTS

| 2,807,618 | 9/1957 | Cislak et al. | 546/254 |
|---|---|---|---|
| 3,728,408 | 4/1973 | Tobias | 546/251 |
| 3,946,020 | 3/1976 | Minato et al. | 546/251 |
| 4,147,874 | 4/1979 | Beschke et al. | 546/251 |
| 4,149,002 | 4/1979 | Beschke et al. | 546/251 |

FOREIGN PATENT DOCUMENTS 2703070  7/1978  Fed. Rep. of Germany .......... 546/251

Primary Examiner—Henry R. Jiles
Assistant Examiner—Robert T. Bond
Attorney, Agent, or Firm—Charles A. Huggett; Raymond W. Barclay

[57] ABSTRACT

A method is provided for synthesizing pyridine or alkylpyridines by reacting ammonia and a carbonyl reactant which is an aldehyde containing 2 to 4 carbon atoms, a ketone containing 3 to 5 carbon atoms or mixtures of said aldehydes and/or ketones under effective conditions in the presence of a catalyst comprising a crystalline aluminosilicate zeolite having a silica to alumina ratio of at least about 12 and a constraint index within the approximate range of 1 to 12 and recovering from the resulting reaction mixture, a product containing at least one compound of pyridine or an alkylpyridine. Addition of methanol and/or formaldehyde to the feed improves selectivity to unsubstituted pyridine.

16 Claims, No Drawings

SYNTHESIS OF PYRIDINE AND ALKYLPYRIDINES

BACKGROUND OF THE INVENTION

1. Field of the Invention

This invention relates to a method for synthesizing pyridine and alkylpyridines by reaction of ammonia and a carbonyl compound selected from the group consisting of aldehydes containing from 2 to 4 carbon atoms and ketones containing from 3 to 5 carbon atoms in the presence of a crystalline aluminosilicate zeolite, characterized by a silica to alumina ratio of at least about 12 and a constraint index, hereinafter defined, in the approximate range of 1 to 12.

2. Description of the Prior Art

The reaction of acetaldehyde or certain other low molecular weight aldehydes and ammonia either in the absence or presence of methanol and/or formaldehyde to yield pyridine and alkyl derivatives thereof has heretofore been carried out in the presence of amorphous silica-alumina composites containing various promoters. See, for example, U.S. Pat. No. 2,807,618. The yields of desired products using the latter catalysts have been poor. Alkylpyridines have also been synthesized, as reported in Advances in Catalysis, Volume 18, page 344 (1968) Academic Press, Inc., New York, N.Y., by passing gaseous acetaldehyde and ammonia over crystalline aluminosilicates, NaX and H-mordenite. While initial conversion utilizing these materials as catalysts was high, catalyst deactivation by coking was rapid, providing a commercially unattractive system, characterized by poor catalytic stability.

SUMMARY OF THE INVENTION

In accordance with the present invention, there is provided a method for synthesizing pyridine and alkylpyridines by reacting ammonia and a carbonyl compound constituting an aldehyde of 2 to 4 carbon atoms or a ketone of 3 to 5 carbon atoms in the presence of a catalyst comprising a particularly defined class of crystalline aluminosilicates which have been found to afford a distinct improvement in selectivity and stability for the production of pyridine and alkyl derivatives thereof over the use of the aforenoted prior art materials.

The crystalline aluminosilicate zeolites employed as catalysts in the present synthesis method are those having a silica to alumina ratio of at least about 12 and a constraint index within the approximate range of 1 to 12. Typical of the zeolites used herein are ZSM-5, ZSM-11, ZSM-12, ZSM-35 and ZSM-38.

The carbonyl reactant taking part in the catalytic reaction described herein may be an aldehyde containing 2 to 4 carbon atoms, a ketone containing 3 to 5 carbon atoms or mixtures of such aldehydes and/or ketones. Representative aldehydes include acetaldehyde, propionaldehyde, acrolein, butyraldehyde and crotonaldehyde. Representative ketones include acetone, methyl ethyl ketone, diethyl ketone and methyl propyl ketone.

Reaction between carbonyl compound and ammonia utilizing the above zeolites as catalysts is effectively carried out at a temperature between about 500° F. and about 1200° F. and preferably between about 700° F. and about 1000° F. at a pressure between about 1 atmosphere and about 100 atmospheres utilizing a liquid hourly space velocity of between about 0.2 and about 20 and preferably between about 0.5 and about 10.

The mole ratio of ammonia to carbonyl reactant in the reaction mixture employed will generally be between about 0.5 and about 10 and more usually between about 1 and about 5. It has further been found that selectivity to pyridine in the product produced may be enhanced by the inclusion in the reaction mixture of methanol and/or formaldehyde. The latter when present as either methanol, formaldehyde or mixtures thereof will generally be in such concentration as to satisfy the following mole ratio relationship:

$$\frac{CH_3OH + CH_2O}{\text{Carbonyl Reactant}} = .5 \text{ to } 2$$

At the completion of the reaction, the product may be separated into its desired components by any feasible means, e.g., by fractionation, to recover a product containing at least one of the pyridine compounds, i.e., pyridine or alkyl derivative thereof.

DESCRIPTION OF SPECIFIC EMBODIMENTS

The catalyst used in the method described herein comprises a crystalline aluminosilicate zeolite which is a member of a novel class of zeolites exhibiting some unusual properties. These zeolites induce profound transformation of aliphatic hydrocarbons to aromatic hydrocarbons in commercially desirable yields and are generally highly effective in conversion reactions involving aromatic hydrocarbons. Although they have unusually low alumina contents, i.e., high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g., of the X and A type.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at a 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| Clinoptilolite | 3.4 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination; with probability, in some instances, of compounding variable extremes.

While the above experimental procedure will enable one to achieve the desired overall conversion of 10 to 60% for most catalyst samples and represents preferred conditions, it may occasionally be necessary to use somewhat more severe conditions for samples of very low activity, such as those having a very high silica to alumina ratio. In those instances, a temperature of up to about 1000° F. and a liquid hourly space velocity of less than one, such as 0.1 or less, can be employed in order to achieve a minimum total conversion of about 10%.

The class of zeolites defined herein is exemplified by ZSM-5, ZSM-11, ZSM-12, ZSM-35 and ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which is incorporated herein by reference.

ZSM-12 is more particularly described in U.S. Pat. No. 3,832,449, the entire contents of which is incorporated herein by reference.

ZSM-35 is more particularly described in U.S. Pat. No. 4,016,245, the entire contents of which is incorporated herein by reference.

ZSM-38 is more particularly described in U.S. Pat. No. 4,046,859, the entire contents of which is incorporated herein by reference.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cation in the forming solution may not be absolutely essential to the formation of this type zeolite; however, the presence of these cations does appear to favor the formation of this special type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35, with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired. Therefore, the preferred zeolites of this invention are those having a constraint index, as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 100 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pykonmeter techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relative small amount of free space within the crystal, which might be expected to result in more stable structures. This free space, however, is important as the locus of catalytic activity.

Crystal framework densities of some typical zeolites are:

| Zeolite | Void Volume | Framework Density |
| --- | --- | --- |
| Ferrierite | 0.28 cc/cc | 1.76 g/cc |
| Mordenite | .28 | 1.7 |
| ZSM-5,-11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

The crystal size of the synthesized zeolite is generally within the approximate range of 0.01 to 40 microns.

When synthesized in the alkali metal form, the zeolite is conveniently converted to the hydrogen form, generally by intermediate formation of the ammonium form as a result of ammonium ion exchange and calcination of ammonium form to yield the hydrogen form. In addition to the hydrogen form, other forms of the zeolite wherein the original alkali metal has been reduced to less than about 1.5 percent by weight may be used. Thus, the original alkali metal of the zeolite or introduced hydrogen cations may be replaced by ion exchange with other suitable ions of Groups IB to VIII of the Periodic Table, including, by way of example, nickel, cadmium, copper, zinc, palladium, calcium or rare earth metals.

It has been found that some of the metal exchanged zeolites, such as HZSM-5 which has undergone exchange with cadmium, are particularly effective in affording improved selectivity with respect to certain desired picoline derivatives, e.g., alpha picoline.

In practicing the desired synthesis method, it may be desirable to incorporate the above-described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays, which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in a raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

The following examples will serve to illustrate the method of the invention without limiting the same:

EXAMPLE 1

A reaction mixture containing 49.5 weight percent acetaldehyde, 5.5 weight percent $NH_3$ and 45.0 weight percent water was passed over a catalyst of HZSM-5 at a temperature of 800° F. and at a liquid hourly space velocity of 1.

After 0.7 hour and 3 hours on stream and fractionation of the resulting product, the following results, set forth in Table I were obtained:

TABLE I

| Time on stream, hrs. | 0.7 | 3.0 |
| --- | --- | --- |
| Acetaldehyde, % Conversion | 93 | 78 |
| Products, Wt. % | | |
| Light products* | 1.1 | 2.4 |
| Pyridine | 7.7 | 5.2 |
| Picolines | 59.6 | 48.7 |
| Lutidines | 20.4 | 34.9 |
| Heavy products | 11.2 | 8.8 |

*Mainly olefins and amines

EXAMPLE 2

A reaction mixture containing 48.4 weight percent acetaldehyde, 16.5 weight percent formaldehyde, 17.6 weight percent methanol, 10.9 weight percent $NH_3$ and 6.6 weight percent water was passed over a catalyst of HZSM-5 at a temperature of 800° F. and a liquid hourly space velocity of 1. For comparison, an identical reaction mixture was passed over a catalyst of H-mordenite under the same reaction conditions.

After 0.5 hour and 3.0 hours on stream and after fractionation of the resulting product, the following results, set forth in Table II were obtained:

TABLE II

| Catalyst | HZSM-5 | | H-Mordenite | |
|---|---|---|---|---|
| Time on stream, hrs. | 0.5 | 3.0 | 0.5 | 3.0 |
| Acetaldehyde, % Conversion | 80 | 60 | 65 | 4 |
| Products, Wt. % | | | | |
| Light products* | 4.1 | 4.5 | 9.5 | 9.3 |
| Pyridine | 44.9 | 45.3 | 28.5 | 9.0 |
| Picolines | 28.1 | 24.5 | 25.2 | 13.9 |
| Lutidines | 17.0 | 19.6 | 27.3 | 33.8 |
| Heavy products | 5.9 | 6.1 | 9.5 | 34.0 |

*Mainly olefins, amines and dimethylether

It will be seen from the above results that use of a ZSM-5 catalyst afforded a distinct improvement in selectivity and stability for pyridine production over comparable use of a catalyst of hydrogen mordenite.

EXAMPLE 3

A reaction mixture containing 49.5 weight percent acetaldehyde, 5.5 weight percent $NH_3$ and 45.0 weight percent water was passed over a catalyst of HZSM-5 at a temperature of 850° F. and a liquid hourly space velocity of 1.

After 2 hours on stream and fractionation of the resulting product, the results hereinafter set forth in Table III were obtained.

EXAMPLE 4

Employing the reaction mixture and reaction conditions of Example 3, a cadmium-containing HZSM-5 catalyst having a cadmium content of 1.02 weight percent was used.

The catalyst was prepared by ion exchanging a composite of 65 weight percent HZSM-5 and 35 weight percent alumina binder with a 4 Normal aqueous solution of $CdCl_2$ for 4 hours at 88° C. The resulting product was then water washed free of chloride, dried at 100° C. and thereafter calcined in air at 528° C.

After 3 hours on stream and fractionation of the resulting product, the results hereinafter set forth in Table III were obtained.

EXAMPLE 5

Employing the reaction mixture and reaction conditions of Example 3, a copper-containing HZSM-5 catalyst having a copper content of 2.8 weight percent was used.

This catalyst was prepared as in Example 4 but wherein the ion exchange solution was a 1 Normal aqueous solution of $CuCl_2$.

After 3 hours on stream and fractionation of the resulting product, the results hereinafter set forth in Table III were obtained.

EXAMPLE 6

Employing the reaction mixture and reaction conditions of Example 3, a nickel-containing HZSM-5 catalyst having a nickel content of 0.7 weight percent was used.

This catalyst was prepared by contacting ammonium exchanged ZSM-5 with a 1 Normal aqueous solution of $Ni(NO_3)_2$ for 4 hours, followed by drying at about 250° F. and calcination in air for 3 hours at 1000° F.

After 5 hours on stream and fractionation of the resulting product, the results set forth in Table III were obtained.

TABLE III

| Catalyst Example | 3 | 4 | 5 | 6 |
|---|---|---|---|---|
| Time on Stream, hrs. | 2 | 3 | 3 | 5 |
| Acetaldehyde, % Conversion | 85 | 89 | 88 | 83 |
| Products, Wt. % | | | | |
| $H_2$, Co, $CO_2$, HCN | 0.5 | 5.4 | 1.8 | 2.2 |
| Hydrocarbons | 27.5 | 17.8 | 16.5 | 28.0 |
| Pyridine | 3.8 | 1.9 | 2.6 | 2.1 |
| 2 Picoline | 12.2 | 12.6 | 11.8 | 11.1 |
| 3&4 Picolines | 15.0 | 13.3 | 15.1 | 13.0 |
| Lutidines | 14.6 | 9.2 | 16.0 | 9.1 |
| 2 Methyl 5 Ethyl Pyridine | 10.3 | 7.9 | 7.9 | 7.5 |
| Heavy Products | 9.6 | 7.8 | 15.8 | 17.3 |
| Acetonitrile | 2.5 | 19.5 | 4.1 | 6.8 |
| Other Aldehydes | 4.1 | 4.8 | 8.4 | 2.9 |

It is to be noted from the above tabulated data that the cadmium exchanged HZSM-5 catalyst of Example 4 was particularly effective in affording increased selectivity with respect to the desired product of 2-picoline.

EXAMPLE 7

A reaction mixture containing 49.2 weight percent acetone, 14.5 weight percent $NH_3$ and 36.3 weight percent water was passed over a HZSM-5 at a temperature of 850° F. and a liquid hourly space velocity of 1.

After three hours on stream and the fractionation of the resulting product, the following results, set forth in Table IV below were obtained:

TABLE IV

| Catalyst | HZSM-5 |
|---|---|
| Time on Stream, hrs. | 3 |
| Acetone, % Conversion | 19 |
| Products Wt. % | |
| $H_2$, CO, HCN | 0.2 |
| Hydrocarbons | 50.8 |
| 2,6 Dimethylpyridine | 2.4 |
| 2,4,6 Trimethylpyridine | 2.8 |
| Heavy products | 0.2 |
| Other Ketones | 0.5 |
| Acetonitrile | 43.1 |

It will be seen from the above results that while the extent of conversion of acetone was, under the specified conditions of reaction, somewhat less than that for acetaldehyde, useful products, including 2,4,6-trimethylpyridine, were obtained.

We claim:

1. A method for synthesizing alpha picoline which comprises effecting reaction between ammonia and a carbonyl reactant selected from the group consisting of aldehydes containing from 2 to 4 carbon atoms, ketones containing from 3 to 5 carbon atoms and mixtures of said aldehydes and ketones under suitable reaction conditions of temperature, pressure and space velocity in the presence of a catalyst comprising a crystalline aluminosilicate zeolite having a silica to alumina ratio of at least about 12 and a constraint index within the approximate range of 1 to 12, which zeolite has been ion exchanged with cadmium and recovering from the resulting reaction mixture, a product containing alpha picoline.

2. The method of claim 1 wherein said reaction is effected in the presence of methanol, formaldehyde or a mixture thereof present in an amount such as to satisfy the following mole ratio relationship:

$$\frac{CH_3OH + CH_2O}{\text{Carbonyl Reactant}} = .5 \text{ to } 2$$

3. The method of claim 1 wherein said reaction conditions include a temperature between about 500° F. and about 1200° F., a pressure between about 1 and about 100 atmospheres and a liquid hourly space velocity between about 0.2 and about 20.

4. The method of claim 1 wherein said reaction conditions include a temperature between about 700° F. and about 1000° F., a pressure between about 1 and about 100 atmospheres and a liquid hourly space velocity of between about 0.5 and about 10.

5. The method of claim 1 wherein the mole ratio of ammonia to carbonyl reactant is between about 0.5 and about 10.

6. The method of claim 1 wherein the mole ratio of ammonia to carbonyl reactant is between about 1 and about 5.

7. The method of claim 1 wherein said crystalline aluminosilicate zeolite is ZSM-5.

8. The method of claim 1 wherein said crystalline aluminosilicate zeolite is HZSM-5.

9. The method of claim 1 wherein said carbonyl reactant is acetaldehyde.

10. The method of claim 1 wherein said carbonyl reactant is acetone.

11. The method of claim 2 wherein said carbonyl reactant is acetaldehyde.

12. The method of claim 2 wherein said carbonyl reactant is acetone.

13. The method of claim 3 wherein said carbonyl reactant is acetaldehyde.

14. The method of claim 3 wherein said carbonyl reactant is acetone.

15. The method of claim 7 wherein said carbonyl reactant is acetaldehyde.

16. The method of claim 7 wherein said carbonyl reactant is acetone.

* * * * *